Figure 1:
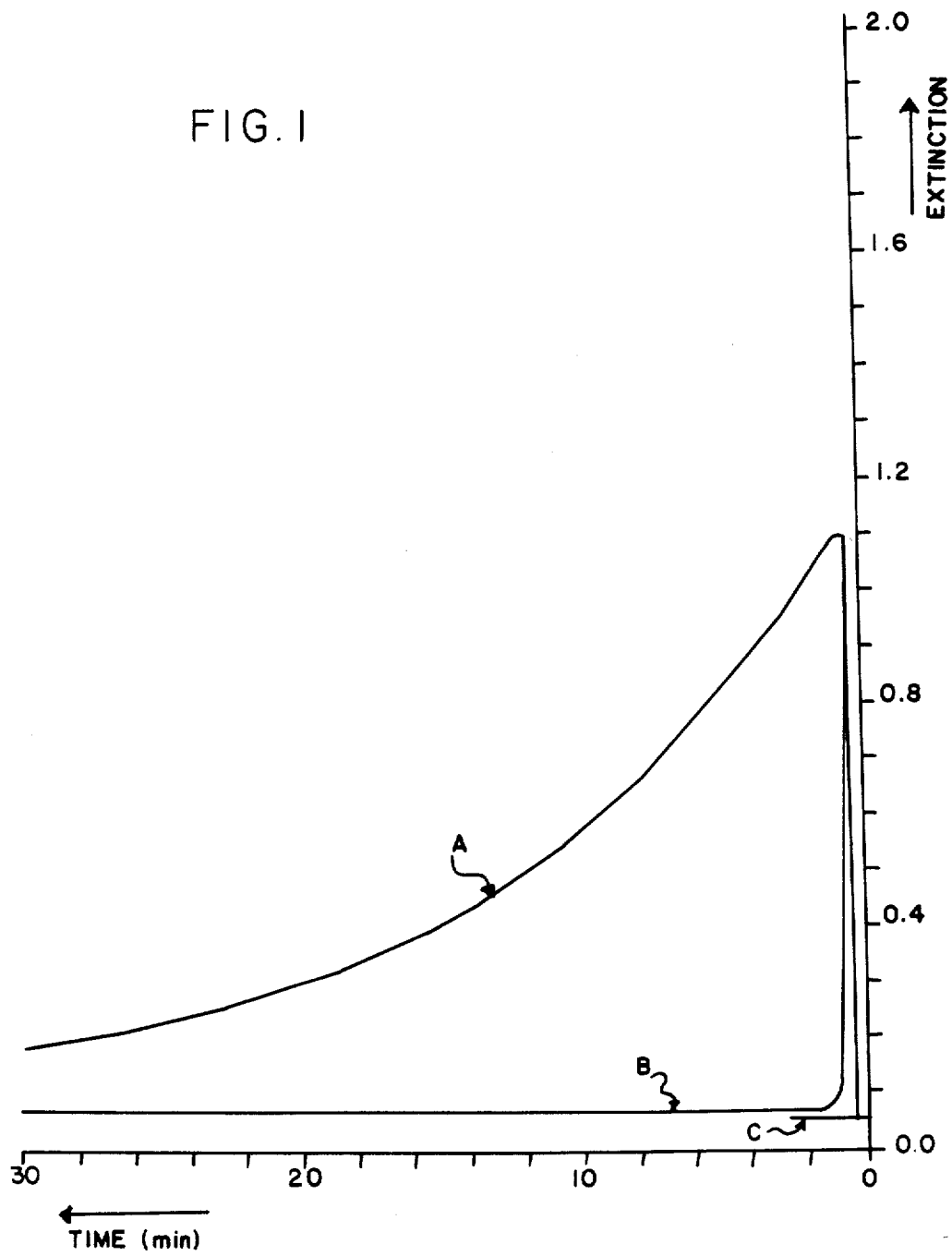

United States Patent [19]

Siedel et al.

[11] Patent Number: 4,708,939
[45] Date of Patent: Nov. 24, 1987

[54] PROCESS AND REAGENT FOR THE COMPLETE AND RAPID REMOVAL OF A TURBIDITY IN A BIOLOGICAL FLUID

[75] Inventors: Joachim Siedel, Bernried; Johnny Staepels; Joachim Ziegenhorn, both of Starnberg, all of Fed. Rep. of Germany

[73] Assignee: Boehringer Mannheim GmbH, Mannheim, Fed. Rep. of Germany

[21] Appl. No.: 803,496

[22] Filed: Dec. 2, 1985

Related U.S. Application Data

[62] Division of Ser. No. 626,633, Jul. 2, 1984, Pat. No. 4,579,825.

[30] Foreign Application Priority Data

Jul. 2, 1983 [DE] Fed. Rep. of Germany ....... 3323949

[51] Int. Cl.$^4$ .................................................. G01N 31/00
[52] U.S. Cl. ............................................ 436/13; 436/17
[58] Field of Search .................. 252/354, 363.5, 408.1; 436/13, 174–176, 17

[56] References Cited

U.S. PATENT DOCUMENTS

| 3,853,465 | 12/1974 | Rush et al. ....................... 252/363.5 |
| 3,955,925 | 5/1976 | Proksch et al. ....................... 436/13 |
| 4,011,045 | 3/1977 | Bonderman ....................... 436/13 |
| 4,184,848 | 1/1980 | Batz et al. . |
| 4,289,469 | 9/1981 | Harders et al. ....................... 436/13 |
| 4,311,788 | 1/1982 | Heuck ....................... 435/7 |
| 4,378,227 | 3/1983 | Batz et al. ....................... 436/17 |
| 4,400,201 | 8/1983 | Milzner ....................... 544/321 |
| 4,551,427 | 11/1985 | Draeger et al. ....................... 435/14 |

*Primary Examiner*—Deborah L. Kyle
*Assistant Examiner*—T. J. Wallen
*Attorney, Agent, or Firm*—Felfe & Lynch

[57] ABSTRACT

The present invention provides an agent for the removal of a turbidity in a biological fluid, wherein it contains (a) a polyethoxylated triglyceride with an HLB value of 4 to 14,
(b) a secondary n-alkane sulphonate, as well as optionally
(c) a futher non- or anionic tenside, in aqueous, optionally buffered solution.

10 Claims, 4 Drawing Figures

PROCESS AND REAGENT FOR THE COMPLETE AND RAPID REMOVAL OF A TURBIDITY IN A BIOLOGICAL FLUID

This is a divisional application of U.S. Ser. No. 626,633 filed July 2, 1984, now U.S. Pat. No. 4,579,825.

The present invention is concerned with a process and agent for the rapid and complete removal of a turbidity in a biological fluid, especially in human blood serum or plasma, with the use of surface-active agents.

Turbidities in human blood serum are brought about by an increased content of triglyceride-rich lipoprotein particles, such as chylomicrons and VLDL (very low density lipoproteins). In this case, one speaks of "lipaemic" or "hyperlipoproteinaemic" serum. Such turbidities represent a considerable problem for the carrying out of photometric analyses of serum components in clinical-chemical diagnosis. This applies especially when the concentration of the component to be determined in the serum is very low, for example in the case of trace elements, and comparatively large amounts of serum must be added to the analysis reagent for a sufficient measurement exactitude (volume ratio serum:analysis reagent $\geq 0.15$). Here, even already in the case of a low degree of lipaemia, the turbidity caused by the serum in the reagent can lead to the exceeding of the linearity range of the photometer and thus considerably impair the measurement or make it impossible.

However, it has also been shown that various immunological test processes, especially those in which the turbidities resulting by immune precipitation reactions are measured nephelometrically or turbidimetrically and in which comparatively small amounts of serum are necessary in the test batch, can be susceptibly disturbed by inherent turbidities of the sample material. As example, there is here mentioned the immuno-nephelometric determination of serum apolipoproteins (Clin. Chem., 28, 5, 1153-1158/1982; Clin. Chem., 29, 1, 120-125/1983), as well as the radioimmunological determination of $\beta$-choriogonadotropin and prostate acid phosphatase (Clin. Chem., 28, 2325/1982).

The complete removal of turbidities (clarification) in lipaemic serum is, therefore, of extraordinary importance for clinical analysis.

Various processes and agents for the removal of turbidities in biological fluids are already known from the literature.

Thus, for example, in Clin. Chem., 29, 120-125/1983, there is described a process in which serum turbidities are removed by shaking out with a mixture of organic solvents. This method requires an additional process step. Furthermore, in the case of strongly lipaemic sera, it can result in uncontrollable volume changes of the sample material and thus in a falsification of the measurement results. Finally, in the case of the use of this process, the determination of serum components which are wholly or partly removed by the extraction is no longer possible.

The same applies to a process in which the turbidity-causing lipoprotein particles are precipitated out by the addition of polyanions, such as phosphotungstic acid/magnesium chloride, to the serum and are centrifuged off (Clin. Chem., 28, 1153-1158/1983).

For reasons of measurement exactitude and of the economy of photometric serum analyses, it is preferable to carry out the clarification directly in the analysis reagent employed for the determination of the particular serum component, namely, completely and within a few minutes ($\leq 10$ min.), as well as usually in a temperature range of from 15° to 40° C.

Such a process, which, however, sometimes only leads to the reduction of the turbidity in a serum or plasma sample, is known, for example, from published Federal Republic of Germany Patent Specification No. 23 27 894 published Dec. 13, 1973. In this case, a high concentration of a polyoxyethylated lauric acid compound is added to the analysis reagent.

In Federal Republic of Germany Patent Specification No. 27 24 757 published Dec. 21, 1978, there is described an agent for the removal of turbidities in serum which consists of an aqueous, buffered solution of fatty acid polyethylene glycol esters, as well as short-chained aliphatic alcohols, glycols or polyethylene glycols or a fatty alcohol-polyglycol ether. This agent can be used for clarifying turbid measurement solutions at a volume ratio of serum:reagent of $= 0.1$ within a few minutes. For example, in the case of a solution with a volume ratio of serum:reagent of 0.1, at 20° to 25° C. a complete clarification takes place within 5 minutes after mixing up. However, in the case of a volume ratio of serum:reagent of $> 0.15$, a considerably longer time is needed for the clarification of the measurement solution. For the removal of the turbidity in a solution with a volume ratio of serum:reagent of 0.16, already 30 minutes are necessary.

From Z. Klin. Chem. Klin. Biochem., 3, 96–99/1965 there is known a process for transferrin-iron determination in serum, wherein a secondary alkyl sulphate ("Teepol 610 S", Shell AG) is added in high concentration to the analysis reagent. In the case of mixing 0.5 ml. serum and 1.4 ml. reagent, a complete turbidity removal is achieved after 15 minutes at ambient temperature.

Finally, in published European Patent Specification No. 0041704 published Dec. 16, 1981, it is suggested to dissolve chylomicrons in aqueous medium with the help of a mixture of a polyethylene glycol ether of an alkanol or alkylaryl alcohol with a branched alkane chain and an HLB value of 12 to 14, a secondary alkyl sulphonate with 10 to 20 carbon atoms in the molecule, as well as optionally an alkali metal p-toluenesulphonate. The testing of an agent described in published European Patent Specification No. 0041704 as being especially useful (agent according to Example 2) showed that it is not possible therewith to achieve a complete clarification within 30 minutes in the case of a strongly lipaemic serum and a volume ratio of serum:reagent of $\geq 0.2$.

These previously known methods for the removal of turbidities in biological fluids thus all still show, in part, considerable disadvantages which essentially depend upon (a) the necessity of a serum pretreatment in an additional process step or, when the clarification takes place directly in the analysis reagent, (b) a limited clarification ability of the agent used, (c) an insufficient clarification speed ($>10$ minutes), as well as (d) a limited pH and temperature range in which the process or agent used is effective, for example when, for the promotion of the clarifying action, lipolytically-active enzymes (lipases) are also added.

Furthermore, in one of the cited literature references is an indication to be found that, in the particular clarification reagent used, antigen-antibody reactions, for example immune precipitation analyses of serum apolipoproteins, can also be carried out free of disturbance.

In order to avoid disturbances by serum turbidities in the case of the immunonephelometric determination of a serum protein, especially of an apolipoprotein, a process is suggested in published Federal Republic of Germany Patent Specification No. 28 29 531 published Jan. 24, 1980 in which the immune reaction is carried out either in the presence of a very low concentration of cationic tenside ($10^{-3}$ to $10^{31\ 1}$ vol.%) or in the presence of a very low concentration of non-ionic tenside ($10^{-3}$ to $10^{-1}$ vol.%) and of a lipolytically-active enzyme. Since only very small amounts of serum must thereby be added to the test batch, high requirements do not have to be demanded of the clarification ability of the agent used.

In the case of analogous immunoturbidimetric measurements, substantially higher serum concentrations are necessary in the test batch. Nothing is stated in published Federal Republic of Germany Patent Specification No. 28 29 531 1/24/80 regarding the effectiveness of the tensides at these increased serum concentrations. However, it is mentioned that, by means of tenside concentrations of over 0.1 vol.%, the immunological reaction between antibody and antigen (in the present case, the apolipoprotein) is inhibited.

Therefore, there is a need for a process and agent which, even in the case of volume ratios of serum:analysis reagent of $\geq 0.15$, bring about a complete and lasting clarification of serum turbidities. The clarification is thereby to take place as quickly as possible, preferably in less than 10 minutes. The effectiveness is to be ensured over the greatest possible pH ($3 \leq pH \leq 9$) and temperature range ($15 \leq T \leq 37°$ C.). Besides the precise determination of trace elements, the process and reagent are also to make possible especially the disturbance-free analysis of proteins, such as apolipoproteins, with immunoturbidimetric measurement methods, even in the case of the use of strongly lipaemic sera. Finally, the agent forming the basis of the process is to be storage-stable over a long period of time, i.e. at least one year at ambient temperature.

Therefore, the object of the present invention is to satisfy this need.

Thus, according to the present invention, there is provided a process for the removal of turbidities in biological fluids by the addition of surface-active agents, wherein, as surface-active agents, there is added
 (a) a polyethoxylated triglyceride with an HLB value of 4 to 14,
 (b) a secondary n-alkane sulphonate, as well as optionally
 (c) a further non- or anionic tenside,
in aqueous, optionally buffered solution.

As polyethoxylated triglyceride, there can be used, for example, polyethoxylated triolein (e.g. Tagat ®, Goldschmidt AG, HLB value 11.3) or polyethoxylated castor oil (e.g. Mulsifan ®RT 7 or Mulsifan ®RT 163, Zschimmer-Schwarz, HLB value about 10 or 6, respectively). Especially good results are achieved when using a polyethoxylated triglyceride which is obtained by the reaction of ethylene oxide and castor oil in an autoclave under alkaline catalysis. The product prepared in this way contains, on average, 10 oxyethylene units per molecule and is commercially available under the name Mulsifan ®RT 163.

The HLB value (hydrophilic-lipophilic balance) of the polyethoxylated triglycerides which can be used according to the present invention can be determined by known processes (cf., for example, Stache "Tensid-Taschenbuch", pub. Carl-Hanser-Verlag, München, Wien, 1979, pages 70–72.

The concentration of the polyethoxylated triglycerides in the aqueous, buffered solution can be 0.5 to 15, preferably 1.0 to 12 and especially 2 to 9 wt.%.

As secondary n-alkane sulphonates, there are preferably used compounds with 12 to 19 carbon atoms in the molecule, either as pure substances or also as mixtures of different n-alkane sulphonates with preponderantly 12 to 19 carbon atoms in the molecule. The secondary n-alkane sulphonates are preferably used as sodium salts. A secondary n-alkane sulphonate (sodium salt) has proved to be especially favourable according to the present invention which is prepared by the sulphoxidation of n-paraffins and has a carbon chain distribution of

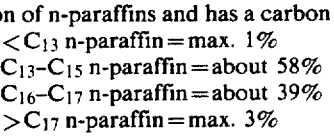

$<C_{13}$ n-paraffin = max. 1%
$C_{13}-C_{15}$ n-paraffin = about 58%
$C_{16}-C_{17}$ n-paraffin = about 39%
$>C_{17}$ n-paraffin = max. 3%

Such a product is commercially available under the name Hostapur ®AT (Hoechst AG) as a water-containing paste with an active material content of 60%.

The secondary n-alkane sulphonate used according to the present invention can be present in the aqueous, optionally buffered solution in a concentration of 0.5 to 10, preferably 1.0 to 7 and especially 1.2 to 4.8 wt.%, referred to the pure active material.

Mixtures of the polyethoxylated triglycerides and secondary n-alkane sulphonates in aqueous, optionally buffered solution already as such bring about a sufficiently rapid clarification of turbid sera. However, for the further acceleration of the speed of clarification, it has proved to be favourable to add a further non- or anionic tenside to these mixtures.

As optionally added further non-ionic tensides, there can be used straight or branched chained alkyl or alkylaryl polyglycol ethers with low degree of oxyethylation (on average 3 to 7 oxyethylene units per molecule). It is preferred to use an isodecanol polyglycol ether with, on average, 5 oxyethylene units per molecule (Lutensol-®ON 50, BASF).

As anionic tensides, there can be used alkylaryl sulphonates, secondary alkyl sulphates or mixtures of alkane sulphonates with 13 to 15 carbon atoms in the molecule and 40 to 50% secondary component (Mersolat ®H, Bayer AG). Sodium dodecylbenzenesulphonate (for example Elfan ®WA 50 with an active material content of 50%, commercially available from Akzo) is especially preferred.

In all cases, concentrations in the aqueous, optionally buffered solution of 0.2 to 5, preferably of 0.5 to 3 and especially of 1 to 2 wt.%, referred to the pure active material, have hereby proved to be favourable.

The process according to the present invention can be carried out by successively mixing the individual components, i.e. water or optionally an aqueous buffer solution, surface-active agents and biological fluid. Preferably, however, there is used a previously prepared mixture of the surface-active agents in an aqueous, optionally buffered solution, which is added to the biological fluid in an amount which leads to a rapid and complete removal of the turbidity. In general, for the complete removal of the turbidity in 0.2 ml. serum, amounts of 0.5 to 2 ml. of the agent according to the present invention suffice.

The pH value of the mixture can be chosen within wide limits. According to the process of the present invention, turbidities can readily be removed at pH values of 3 to 9. For the adjustment of the pH value, there can be used all available buffer substances, the pK value of which is from 2.0 to 10.0. Especially preferred are succinate, acetate, phosphate and tris buffers. The buffer concentration is preferably from 5 to 250 mM and especially from 10 to 170 mM.

The speed of clarification can, to a certain extent, be favourably influenced by an increase of the ionic strength in the aqueous, optionally buffered medium. Therefore, it has proved to be preferable, in the case of the absence of buffer substance or in the case of low buffer concentrations (5 to 20 mM), to add a salt, for example sodium chloride, or several salts to the biological fluid or to the detergent mixture. The concentration of added salt is preferably from 50 to 200 mM and especially from 50 to 150 mM.

The turbidity removal takes place, by the process according to the present invention, over a wide temperature range ($15°$ C.$\leq$T$\leq$$40°$ C.) but preferably at a temperature of from 20° to 37° C.

The present invention also provides an agent for the rapid and complete removal of a turbidity in a biological fluid, especially in human blood serum or plasma, wherein it contains (a) a polyethoxylated triglyceride with an HLB value of 4 to 14, (b) a secondary n-alkane sulphonate, as well as optionally (c) a further non- or anionic tenside, in aqueous, optionally buffered solution.

The agent according to the present invention preferably contains in aqueous buffered solution (a) 0.5 to 15 and preferably 1.0 to 12 wt.% polyethoxylated triglyceride with an HLB value of 4 to 14, (b) 0.5 to 10 and preferably 1.0 to 7 wt.% of secondary n-alkane sulphonate, as well as optionally (c) 0.2 to 5 and preferably 0.5 to 3 wt.% of a further non- or anionic tenside.

An agent of the following composition is especially preferred:

(a) 2 to 9 wt.% polyethoxylated triolein or castor oil, (b) 1.2 to 4.8 wt.% of a secondary n-alkane sulphonate with 12 to 19 carbon atoms in the molecule or a mixture of various secondary n-alkane sulphonates with preponderantly 12 to 19 carbon atoms in the molecule, as well as optionally (c) 1 to 2 wt.% of a straight or branched chained alkyl or alkylaryl polyglycol ether with, on average, 3 to 7 oxyethylene units per molecule, of an alkyl-aryl sulphonate, secondary alkyl sulphate or of a mixture of alkane sulphonates with 13 to 15 carbon atoms in the molecule and 40 to 50% secondary component, in aqueous, optionally buffered solution.

As buffer, the agent according to the present invention can contain generally known buffer substances, the pK value of which is from 2.0 to 10.0, succinate, acetate, phosphate or tris buffer being especially preferred. The buffer concentration can be from 5 to 250 and preferably 10 to 170 mM.

Furthermore, for increasing the ionic strength, the agent according to the present invention can contain a salt, for example sodium chloride, or several salts. The salt concentration is preferably from 50 to 200 mM and especially from 50 to 150 mM.

In addition to the mentioned components, the reagent can contain further substances which are necessary for the photometric analysis of a particular serum component. In the case of trace element analysis, for example of serum transferrin iron, this can be a reducing agent, such as ascorbic acid, as well as a colour complex former, such as bathophen-anthroline-disulphonic acid, FerroZine ® or some other compound of the ferroin type.

For the immunoturbidimetric or -nephelometric determination of serum components, for example apolipoproteins and their subunits, as well as of immunologically-active apolipoprotein fission fragments, as additional components the reagent can contain antibodies, for example in the form of an antiserum, the gamma-globulin or IgG fractions obtained therefrom, or also monoclonal antibodies, as well as a substance which promotes the immune precipitation reaction, such as polyethylene glycol with a molecular weight from 1000 to 10,000 and preferably of 6000, in a concentration of 1 to 6 and preferably of 3 to 4 wt.%.

The process and reagent according to the present invention for the rapid and complete removal of turbidities in biological fluids is, with regard to its clarifying action, markedly superior to the known processes and available agents, especially in the case of volume ratios of serum:reagent$\geq$0.15. The superiority shows itself especially clearly in the case of the analysis of trace elements in serum, for example in the determination of iron in serum. In order to achieve a sufficient measurement exactitude, in relationship to the analysis reagent, large amounts of serum must hereby be used, i.e. in the measurement solution, there is to be reckoned with a high lipid content and thus a stronger appearance of turbidity. Due to the high clarification speed, also in strongly lipaemic sera, analyses of particular components can be carried out within a maximum of 10 minutes after mixing the serum and reagent, which is especially important for the automated analysis.

Furthermore, it is surprising that, in spite of the detergent concentration in the described reagent, which is high in comparison with the agent claimed in published Federal Republic of Germany Patent Specification No. 28 29 531, immunological determinations of serum components can also be carried out satisfactorily via antigen-antibody precipitation reactions. Therefore, the process and reagent according to the present invention can also be used in advantageous manner in such immunological precipitation reactions, for example in the immunological determination of serum apolipoproteins or of their subunits or of immunologically-active apolipoprotein fragments.

The accompanying drawings illustrate:

FIG. 1: the rate of the turbidity removal in a strongly lipaemic serum with various clarification agents according to Example 1.

A: Reagent=agent according to published European Patent Specification No. 0 041 704

B: Reagent B=agent according to the present invention

C: Reagent blank

Volume ratio serum:analysis reagent=0.2;

temperature=25° C.; $\lambda$=578 nm; layer thickness=1 cm.

Figure 2:
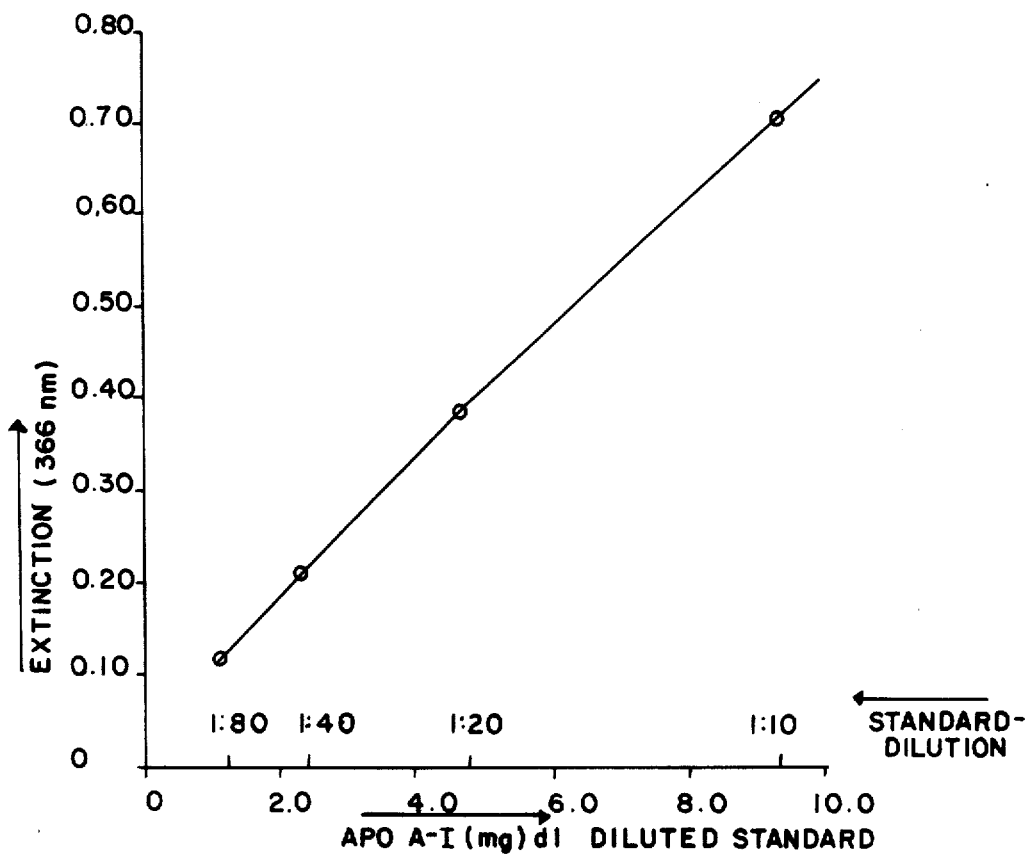

FIG. 2: the immunoturbidimetric determination of serum apolipoprotein A-I (APO A-I); calibration curve determined via standard serum dilution series. Measurement corresponding to Example 3.

Figure 3:
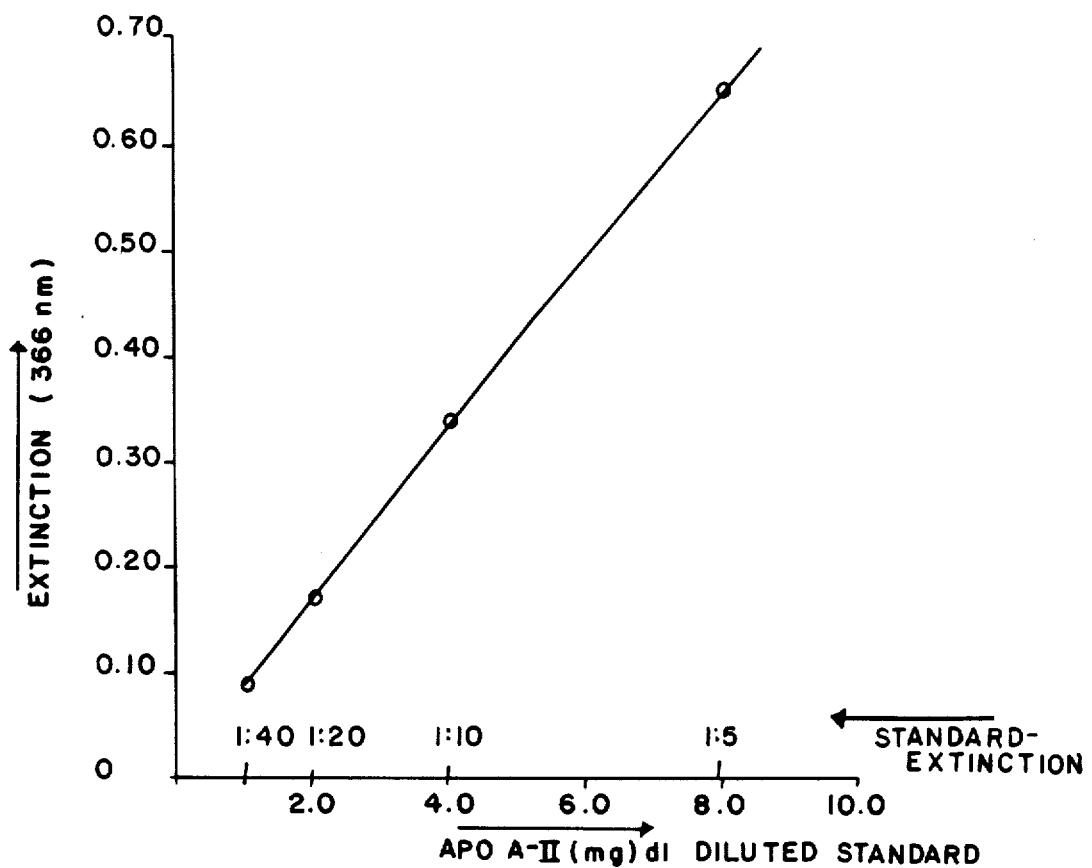

FIG. 3: the immunoturbidimetric determination of serum apolipoprotein A-II (APO A-II); calibration curve determined via standard serum dilution series. Measurement corresponding to Example 3.

Figure 4:
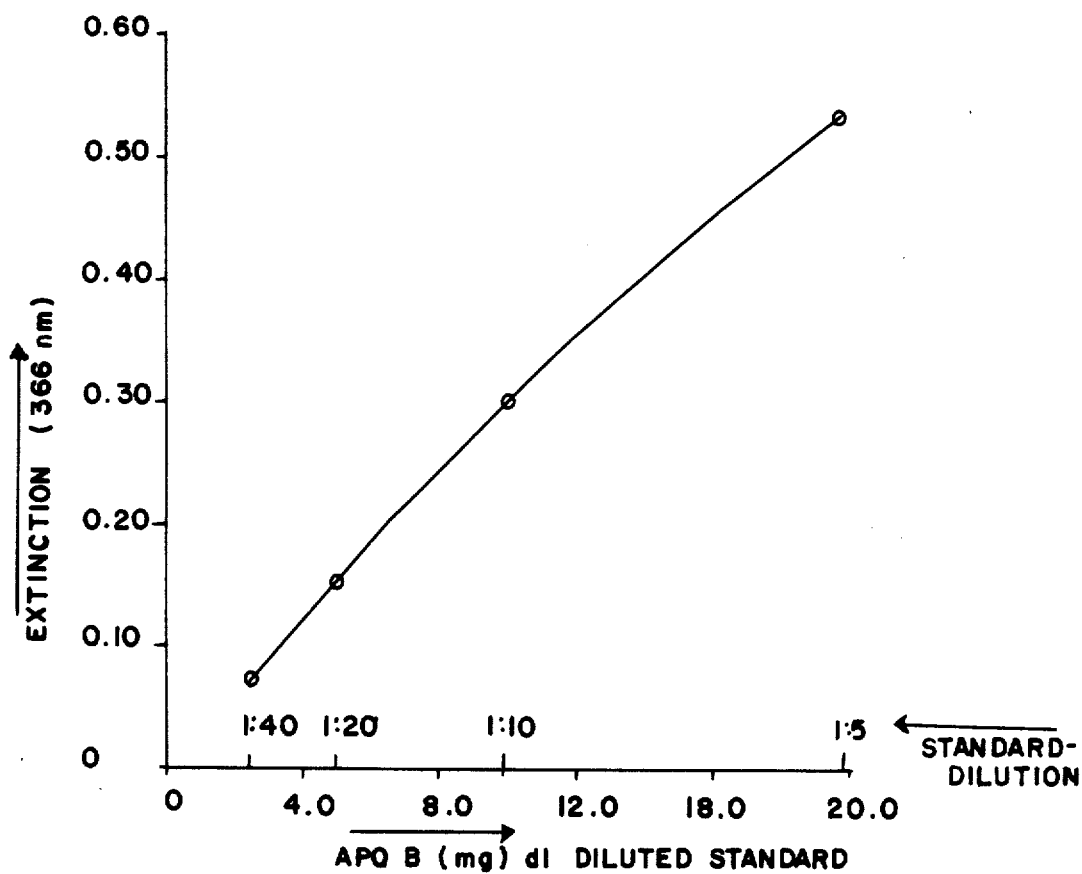

FIG. 4: immunoturbidimetric determination of serum apolipoprotein B (APO B); calibration curve determined via standard serum dilution series. Measurement corresponding to Example 3.

The following Examples are given for the purpose of illustrating the present invention:

EXAMPLE 1

Clarification speed of a lipaemic serum with reagents containing different surface-active agents

1. Reagents

Reagent A (agent according to published European Patent Specification No. 0 041 704)

| component material | concentration |
|---|---|
| Mersolat$^R$ H, 30% in $H_2O$ | 150 ml./liter |
| Triton$^R$ × 151, 30% in $H_2O$ | 200 ml./liter |
| p-toluenesulphonic acid, sodium salt | 258 mmol/liter |

Mersolat ®H = commercially available mixture of secondary alkane sulphonates with 13 to 15 carbon atoms and 40 to 50% secondary component Triton ®×15-1 = isooctylphenyl polyethylene glycol ether.

Reagent B (agent according to the present invention

| component material | concentration |
|---|---|
| Mulsifan$^R$ RT 163 | 90.00 g./liter (= 9.0 wt. %) |
| Hostapur$^R$ AT | 80.00 g./liter (= 4.8 wt. %) |
| Elfan$^R$ WA 50 | 40.00 g./liter (= 2.0 wt. %) |
| sodium acetate buffer (pH 5.4) | 170 mmol/liter |

2. Carrying out of the test

In a 1 cm. cuvette, 0.2 ml. of a strongly lipaemic serum are mixed at 25° C. with 1 ml. of Reagent A or Reagent B. The change of the transparency at 578 nm is determined in dependence upon the time. The results obtained are illustrated graphically in FIG. 1.

3. Evaluation

The course of change of the transparency illustrated in FIG. 1 shows that, in the case of a serum:analysis reagent ratio of 0.2, with the agent according to the present invention (Reagent B), already after 2 minutes a complete removal of the turbidity has been achieved. With the reagent according to published European Patent Specification No. 0 041 704, the turbidity is still not completely removed even after 30 minutes.

EXAMPLE 2 (Example of use):

Determination of iron in serum

1. Reagents

1.1 Blank reagent

| component material | concentration |
|---|---|
| Mulsifan$^R$ RT 163 | 90.00 g./liter |
| | (= 9.0 wt. %) |
| Hostapur$^R$ AT | 80.00 g./liter |
| | (= 4.8 wt. %) |
| Elfan$^R$ WA 50 | 40.00 g./liter |
| | (= 2.0 wt. %) |
| sodium acetate buffer (pH 5.4) | 170 mmol/liter |
| ascorbic acid | 10 mmol/liter |

1.2 Colour reagent

| component material | concentration |
|---|---|
| Mulsifan$^R$ RT 163 | 90.00 g./liter |
| | (= 9.0 wt. %) |
| Hostapur$^R$ AT | 80.00 g./liter |
| | (= 4.8 wt. %) |
| Elfan$^R$ WA 50 | 40.00 g./liter |
| | (= 2.0 wt. %) |
| sodium acetate buffer (pH 5.4) | 170 mmol/liter |
| ascorbic acid | 10 mmol/liter |
| FerroZine$^R$ [1] | 1.6 mmol/liter |

[1] Registered Trade Mark of the Hach Chemical Co., Ames, Iowa, USA.

2. Test batch

Temperature: 37° C.; wavelength: 578 nm; layer thickness: 10 mm.

The following solutions are pipetted into iron-free reaction vessels:

| | sample | sample blank |
|---|---|---|
| colour reagent | 1.00 ml. | — |
| reagent blank | — | 1.00 ml. |
| serum | 0.20 ml. | 0.20 ml. |

In each case, the components are mixed and incubated for 10 minutes, whereafter the absorption of the sample is measured against a mixture of 1.00 ml. colour reagent and 0.20 ml. water ($\Delta A_1$), as well as of sample blank against a mixture of 1.00 ml. reagent blank and 0.20 ml. water ($\Delta A_2$). From this is calculated $\Delta A = \Delta A_1 - \Delta A_2$.

3. Evaluation

The concentration of iron in the serum is calculated according to the following equation: concentration of iron in the serum ($\mu$g./100 ml.) = $\Delta A \times 1330$.

Instead of Mulsifan ® RT 163, in Reagents 1.1 and 1.2 there can be used Mulsifan ® RT 7 in the same amounts, without changing the result. In the same way, Elfan ® WA 50 (sodium dodecylbenzenesulphonate, 50% active material content in aqueous solution) can be replaced by an equal concentration (referred to the active material portion) of secondary alkyl sulphate (Teepol ® 610 S, Firm Shell) (8 to 18 carbon atoms in the molecule). In all cases, with the use of lipaemic serum, the clarification is concluded and complete within the incubation period.

EXAMPLE 3 (Example of use):

Determination of apolipoproteins (A-I, A-II and B) in serum

1. Reagents 1.1 Sheep anti-human Apo-A-I-antiserum (gamma globulin fraction, Boehringer Mannheim GmbH, Cat. No. 726 478)

1.2 Sheep anti-human Apo-A-II-antiserum (gamma globulin fraction, Boehringer Mannheim GmbH, Cat. No. 726 486)

1.3 Sheep anti-human Apo-B-antiserum (gamma globulin fraction, Boehringer Mannheim GmbH, Cat. No. 726 494)

1.4 Antiserum diluent

| Composition | |
|---|---|
| component material | concentration |
| Mulsifan$^R$ RT 163 | 20 g./liter (= 2.0 wt. %) |
| Hostapur$^R$ AT | 20 g./liter (= 1.2 wt. %) |
| Lutensol$^R$ ON 50 | 10 g./liter (= 1.0 wt. %) |
| potassium phosphate buffer (pH 7.4) | 10 mmol/liter |
| sodium chloride | 150 mmol/liter |
| polyethylene glycol 6000 | 40 g./liter |

1.5 Sample diluent (for serum or standard); potassium phosphate buffer (pH 7.4) 10 mmol/liter, sodium chloride 150 mmol/liter 1.6 Standard serum (Immunoneph ® Reference Standard, Immuno GmbH, Cat. No. 4380105)

2. Antiserum, standard serum and serum dilution 2.1 Antiserum dilution

Antiserum (1.1, 1.2 or 1.3) in each case diluted 10 fold with serum diluent 1.4. Before use, leave to stand for 15 minutes at 20°-25° C.

2.2 Standard serum dilution

Standard serum (1.6) dilute 5, 10, 20, 40 and 80 fold with sample diluent (1.5).

2.3 Serum dilution

For Apo-A-I determination dilute serum 20 fold, for Apo-II or Apo B determination dilute serum 10 fold with sample diluent (1.5).

3. Test batch (for either Apo A-I, Apo A-II or Apo-B) Temperature: 25° C.; wavelength: 366 nm; layer thickness: 10 mm.

Into the reaction vessel is pipetted:

| | sample | sample blank |
|---|---|---|
| antiserum dilution | 2.00 ml. | — |
| antiserum diluent | — | 2.00 ml. |
| serum or standard serum dilution | 0.10 ml. | 0.10 ml. |

The components are mixed, incubated for 2.5 hours and briefly shaken up and the absorption of the sample is measured against a mixture of 2.00 ml. antiserum dilution and 0.10 ml. sample diluent ($\Delta A_1$), as well as of the sample blank against a mixture of 2.00 ml. antiserum diluent and 0.10 ml. serum or standard dilution ($\Delta A_2$). From this is calculated $\Delta A = \Delta A_1 - \Delta A_2$.

4. Evaluation

The concentration of either Apo A-I, Apo A-II or Apo B with $\Delta A$ is determined via the reference curves produced with the standard dilution series. Typical reference curves obtained with this test process are illustrated in FIGS. 2 to 4 of the accompanying drawings.

Instead of Mulsifan ® RT 163, in the antiserum diluent 1.4 there can also be used Mulsifan ® RT 7 or polyethoxylated triolein (e.g. Tagat ® TO) in the same amounts, without the results changing. In all cases, the clarification of lipaemic sera is completely concluded in a short time (about 1 minute), as can be determined via a sample blank batch.

It will be understood that the specification and examples are illustrative but not limitative of the present invention and that other embodiments within the spirit and scope of the invention will suggest themselves to those skilled in the art.

What is claimed is:

1. An agent for the removal of turbidity in a biological fluid, comprising
   (a) 0.5 to 15 wt.% of a polyethoxylated triglyceride with an HLB value of 4 to 14, and
   (b) 0.5 to 10 wt.% of a secondary n-alkane sulphonate in aqueous solution.

2. The agent of claim 1 further comprising a further non- or anionic tenside.

3. The agent of claim 1 wherein the aqueous solution is buffered.

4. The agent of claim 1, comprising
   (a) 2 to 9 wt.% polyethoxylated triolein or polyethoxylated castor oil, and
   (b) 1.2 to 4.8 wt.% of a secondary n-alkane sulphonate with 12 to 19 carbon atoms in the molecule or a mixture of various secondary n-alkane sulphonates with 12 to 19 carbon atoms in the molecule.

5. The agent of claim 4 further comprising 1 to 2 wt.% of a straight or branched chain alkyl or alkylaryl polyglycol ether with, on average, 3 to 7 oxyethylene units per molecule, of an alkylaryl sulphonate, secondary alkyl sulphate or of a mixture of alkane sulphonates with 13 to 15 carbon atoms in the molecule and 40 to 50% of secondary component, in aqueous solution.

6. The agent of claim 1 wherein the aqueous solution contains a buffer with a pK value of between 2.0 and 10.0.

7. The agent of claim 6 wherein the buffer is a succinate, acetate, phosphate or tris buffer in a concentration of 5 to 250 mM.

8. The agent of claim 1 further comprising at least one salt to increase the ionic strength of the solution.

9. The agent of claim 8 wherein the salt is sodium chloride in a concentration of 50 to 200 mM.

10. The agent of claim 1 further comprising 0.2 to 5 wt.% of a further non- or anionic tenside.

* * * * *

UNITED STATES PATENT AND TRADEMARK OFFICE
CERTIFICATE OF CORRECTION

PATENT NO. : 4,708,939

DATED : November 24, 1987

INVENTOR(S) : Joachim Siedel, et al.

It is certified that error appears in the above-identified patent and that said Letters Patent is hereby corrected as shown below:

Column 2, line 20: change "=" to -- $\leftarrow$ --.

Column 3, line 11: change "$10^{311}$" to -- $10^{-1}$ --.

Column 6, line 59: after "Reagent" add -- A --.

Column 7, lines 31-2: change "15-1" to -- 151 --.

Signed and Sealed this

Fifth Day of July, 1988

Attest:

DONALD J. QUIGG

Attesting Officer

Commissioner of Patents and Trademarks